United States Patent
Song et al.

(10) Patent No.: US 9,309,570 B2
(45) Date of Patent: Apr. 12, 2016

(54) METHOD AND DEVICE FOR GENETIC MAP CONSTRUCTION, METHOD AND DEVICE FOR HAPLOTYPE ANALYSIS

(75) Inventors: Luting Song, Shenzhen (CN); Di Shao, Shenzhen (CN); Zequn Zheng, Shenzhen (CN); Zhijun Zheng, Shenzhen (CN); Kui Wu, Shenzhen (CN); Shuheng Liang, Shenzhen (CN); Ye Tao, Shenzhen (CN); Yong Hou, Shenzhen (CN)

(73) Assignee: BGI TECH SOLUTIONS CO., LTD., Shenzhen (CN)

( * ) Notice: Subject to any disclaimer, the term of this patent is extended or adjusted under 35 U.S.C. 154(b) by 0 days.

(21) Appl. No.: 14/240,955

(22) PCT Filed: Aug. 24, 2012

(86) PCT No.: PCT/CN2012/080574
§ 371 (c)(1),
(2), (4) Date: Feb. 25, 2014

(87) PCT Pub. No.: WO2013/029502
PCT Pub. Date: Mar. 7, 2013

(65) Prior Publication Data
US 2014/0194300 A1    Jul. 10, 2014

(30) Foreign Application Priority Data
Aug. 26, 2011  (CN) .......................... 2011 1 0246888

(51) Int. Cl.
| | |
|---|---|
| *C12Q 1/68* | (2006.01) |
| *C12M 1/34* | (2006.01) |
| *G01N 33/48* | (2006.01) |
| *G06F 19/20* | (2011.01) |
| *G06F 19/22* | (2011.01) |

(52) U.S. Cl.
CPC ............ *C12Q 1/6869* (2013.01); *C12Q 1/6874* (2013.01); *C12Q 1/6881* (2013.01); *C12Q 2600/172* (2013.01); *G06F 19/20* (2013.01); *G06F 19/22* (2013.01)

(58) Field of Classification Search
None
See application file for complete search history.

(56) References Cited

PUBLICATIONS

General Zoology, Fourth Edition, (1965) Storer et al, McGraw-Hill Book Company, New York, p. 193.*
Friedman, The World is Flat, 2005, Farrar, Straus and Giroux, New York, pp. 94-95.*
International Search Report and Written Opinion for PCT/CN2012/080574 completed Nov. 12, 2012 by State Intellectual Property Office of the P.R. China.
Xie WB et al., Patent-independent genotyping for constructing an ultrahigh-density linkage map based on population sequencing, PNAS, Jun. 8, 2010, vol. 107, No. 23, pp. 10578-10583.
Jiang ZW et al., Genome amplification of single sperm using multiple displacement amplification, Nucleic Acids Research, Jun. 7, 2005, vol. 33, No. 10, e91.

* cited by examiner

*Primary Examiner* — James Martinell
(74) *Attorney, Agent, or Firm* — Westman, Champlin & Koehler, P.A.; Z. Peter Sawicki; Amanda Prose

(57) ABSTRACT

Provided are the method and device for genetic map construction and the method and device for haplotype determination of a single cell. Wherein the method for genetic map construction includes: whole genome sequencing for at least a single cell from a same species, aligning the sequencing data to reference sequences respectively to determine genotypes of SNP sites, determining male parent a/female parent b typing results of SNP genotypes of a single cell based on the genotypes of SNP sites, dividing the chromosome of the species into linkage regions based on the male parent a/female parent b typing results of SNP genotypes, determining the variation ratio of a/b between two linkage regions to obtain recombination rate between every two continuous linkage regions, determining recombination map of a single cell according to the recombination rate, wherein the boundary site of a and b is the recombination site, determining the recombination rate of each recombination rate based on the recombination map to construct a genetic map of the species.

17 Claims, 5 Drawing Sheets

METHOD AND DEVICE FOR GENETIC MAP CONSTRUCTION, METHOD AND DEVICE FOR HAPLOTYPE ANALYSIS

CROSS-REFERENCE TO RELATED APPLICATION

This application is a Section 371 National Stage Application of International Application No. PCT/CN2012/080574, filed Aug. 24, 2012, and published as WO/2013/029502 on Mar. 7, 2013, in Chinese, which claims priority to and benefits of Chinese Patent Application Serial No. 201110246888.3, filed with the State Intellectual Property Office of P. R. China on Aug. 26, 2011, the entire contents of which are incorporated herein by reference in their entirety.

FIELD

The present disclosure relates to a field of genetics and bioinformatics, and more particularly to a field of a method and a device of constructing a genetic map, as well as a method and a device of determining a haplotype of a single cell.

BACKGROUND

A construction of the genetic map is based on the third law of genetics—law of linkage and crossing-over, i.e. a genetic map taking a genetic marker having a genetic polymorphism as a "sign", and taking a genetic distance (a percentage of crossing-over and recombination between two sites in a meiotic event, 1% of a recombination rate is known as 1 cm) as a map distance. The construction of the genetic map has great implications for various species researches, which can elaborate genetic laws and characteristics of the species. Using this function, many genetic laws of a biological function related to human can be studied. For example, in the study of crops, the construction of the genetic map can enable us to acknowledge a genetic recombination rule of high-yield crops or anti-disease-related gene, which can give a guidance for breeding works to obtain a high-yield product with a strong patience; however for humanity itself, the construction of the genetic map can better enable us to study a certain genetic diseases, as well as give a guidance for eugenics.

However, the tradition methods of constructing the current genetic map cannot well applied to human beings. Because the construction of the genetic map is based on a statistical analysis of randomly allocating a homologous recombination event produced in meiosis to a progeny individual, a plenty of individuals of every progeny needs to be selected to study, however, the mammal lacks of a plenty of progenies for constructing a map, which directly restricts a process of constructing the human genetic map, since it is difficult to select such a large family to meet a randomness condition in statistics for study. N. ARNHEIM, H. LI et al. use a single sperm to construct a genetic map (Genetic mapping by single sperm typing, *Animal Genetics* 1991, 22, 105-115), which solves a problem of a sample selection, however, there is still a significant limitation. The method used herein can only amplify a part of known genes for subsequent analysis, which not only depends on primer effects, but also can do nothing regarding unknown genes and fragments which are not easy to amplify, thus, the genetic map obtained by such method is relatively one-sided and deficient.

A Next-Generation high-throughput sequencing technique represented by Illumina Solexa, ABI SOLiD and Roche 454, and a Third sequencing technique (i.e. a single molecule sequencing technique), mainly comprise: real single molecule sequencing technology of Helicos company, single molecule real time sequencing technology of Pacific Biosciences company, nanopore sequencing technology of Oxford Nanopore Technologies company, and et al., which have developed fast in the recent years and become important tools for genetics study.

SUMMARY

Embodiments of the present disclosure seek to solve at least one of the problems existing in the prior art to at least some extent. To this end, the present disclosure provides a method and a device of constructing a genetic map, as well as a method and a device of determining a a haplotype of a single cell.

According to embodiments of a first broad aspect of the present disclosure, there is provided a method of constructing a genetic map.

According to embodiments of the present disclosure, the method may comprise following steps: whole genome sequencing for at least one single cell derived from a same species, to obtain every whole genome sequencing data of the at least one single cell; aligning the every whole genome sequencing data of the at least one single cell to a reference sequence respectively, to determine every SNP site genotypes of the at least one single cell; based on the every SNP site genotypes of the at least one single cell, deducing genotypes of two chromosomes from a male parent and a female parent respectively by means of a maximum parsimony of recombination, to determine male parent a/female parent b typing results of every SNP genotype of the at least one single cell; based on the male parent a/female parent b typing results of every SNP genotype of the at least one single cell, dividing a chromosome of the species into linkage regions, wherein a standard of dividing the chromosome of the species into linkage regions is that: (1) the SNP number comprising continuous same a or b is at least 5; (2) a physical length of a selected linkage region is greater than 250 kb; for every one of the at least one single cell, determining a variation ratio of a/b between two continuous linkage regions, to obtain a recombination rate between every two continuous linkage regions; based on the recombination rate between every two continuous linkage regions, determining every recombination map of the at least one single cell, wherein a boundary site between a and b is a recombination site; and based on recombination maps of all single cells, determining a recombination rate of each recombination site, to construct the genetic map of the species. The method of constructing the genetic map of the present disclosure can be used to effectively construct a mammal genetic map, particularly the human genetic map.

According to embodiments of the present disclosure, in the method of constructing the genetic map of the present disclosure, kinds of the species are not subjected to special restrictions, according to some specific examples of the present disclosure, the species is a mammal. According to other embodiments of the present disclosure, preferably, the mammal is human.

According to embodiments of the present disclosure, in the method of constructing the genetic map of the present disclosure, the single cell is a germ cell. According to some specific examples of the present disclosure, the germ cell is a sperm cell.

According to embodiments of the present disclosure, in the method of constructing the genetic map of the present disclosure, methods and platforms for the whole genome sequencing are not subjected to special restrictions, according to some specific examples of the present disclosure, the whole genome sequencing may be performed using a Next-Generation or a Third-Generation sequencing platform.

According to embodiments of the present disclosure, in the method of constructing the genetic map of the present disclosure, the step of whole genome sequencing for at least one single cell derived from a same species further comprises: lysing the single cell to release a whole genome DNA using an alkaline lysis method; amplifying the whole genome DNA, to obtain an amplified whole genome DNA; for the amplified whole genome DNA, constructing a sequencing-library, to obtain a sequencing-library of the single cell; and sequencing the sequencing-library of the single cell, to obtain the every whole genome sequencing data of the at least one single cell.

According to embodiments of the present disclosure, in the method of constructing the genetic map of the present disclosure, the single cell is a sperm cell, and the released whole genome DNA is subjected to a guanidine hydrochloride treatment after the single cell is lysed to release a whole genome DNA. According to some specific examples of the present disclosure, the guanidine hydrochloride treatment is performed using a solution of guanidine hydrochloride having a concentration of $2 \times 10^{-3}$ to $3 \times 10^{-1}$ mol/L. According to other embodiments of the present disclosure, in the method of constructing the genetic map of the present disclosure, the species is human, and the solution of guanidine hydrochloride having a final concentration of $2 \times 10^{-3}$ mol/L.

According to embodiments of the present disclosure, in the method of constructing the genetic map of the present disclosure, the reference sequence is a known genomic sequence of the species.

According to embodiments of a second broad aspect of the present disclosure, there is provided a device of constructing a genetic map. According to embodiments of the present disclosure, the device may comprise: a single cell whole genome sequencing unit, for whole genome sequencing for at least one single cell derived from a same species, to obtain every whole genome sequencing data of the at least one single cell; an SNP site genotype statistical unit, connected to the single cell whole genome sequencing unit, for aligning the every whole genome sequencing data of the at least one single cell to a reference sequence respectively, to determine every SNP site genotypes of the at least one single cell; a parent typing unit, connected to the SNP site genotype statistical unit, for based on the every SNP site genotypes of the at least one single cell, deducing genotypes of two chromosomes from a male parent and a female parent respectively by means of a maximum parsimony of recombination, to determine male parent a/female parent b typing results of every SNP genotype of the at least one single cell; a linkage region dividing unit, connected to the parent typing unit, for dividing a chromosome of the species into linkage regions based on the male parent a/female parent b typing results of every SNP genotype of the at least one single cell, wherein a standard of dividing the chromosome of the species into linkage regions is that: (1) the SNP number comprising continuous same a or b is at least 5; (2) a physical length of a selected linkage region is greater than 250 kb; a recombination rate between contiguous linkage regions calculating unit, connected to the linkage region dividing unit, for every one of the at least one single cell, determining a variation ratio of a/b between two continuous linkage regions, to obtain a recombination rate between every two continuous linkage regions, and based on the recombination rate between every two continuous linkage regions, determining every recombination map of the at least one single cell, wherein a boundary site between a and b is a recombination site; a recombination rate of the recombination site calculating unit, connected to the recombination rate between contiguous linkage regions calculating unit, for based on recombination maps of all single cells, determining a recombination rate of each recombination site, to construct the genetic map of the species. The device of constructing the genetic map of the present disclosure may be used to effectively construct a mammal genetic map, particularly the human genetic map.

According to embodiments of the present disclosure, in the device of constructing the genetic map of the present disclosure, the single cell whole genome sequencing unit may further comprise: a cellular whole genome DNA obtaining subunit, for lysing the single cell to release a whole genome DNA using an alkaline lysis method; a whole genome DNA amplifying subunit, connected to the cellular whole genome DNA obtaining subunit, for amplifying the whole genome DNA, to obtain an amplified whole genome DNA; and a whole genome DNA sequencing subunit, connected to the whole genome DNA amplifying subunit, for constructing a sequencing-library for the amplified whole genome DNA, to obtain a sequencing-library of the single cell, and sequencing the sequencing-library of the single cell, to obtain the every whole genome sequencing data of the at least one single cell.

According to embodiments of the present disclosure, in the device of constructing the genetic map of the present disclosure, the cellular whole genome DNA obtaining subunit is further suitable for subjecting the released whole genome DNA to a guanidine hydrochloride treatment after the single cell is lysed to release a whole genome DNA.

According to embodiments of the present disclosure, in the device of constructing the genetic map of the present disclosure, platforms can be used as the whole genome DNA sequencing subunit are not subjected special restrictions, according to some special examples of the present disclosure, the whole genome DNA sequencing subunit is suitable for using at least one of a Next-Generation and a Third-Generation sequencing platform.

According to embodiments of a third broad aspect of the present disclosure, there is provided a method of determining a haplotype of a single cell. According to embodiments of the present disclosure, the method may comprise following steps: whole genome sequencing the single cell, to obtain a whole genome sequencing data of the single cell; aligning the obtained whole genome sequencing data to a reference sequence, to determine SNP site genotypes of the single cell; based on the SNP site genotypes of the single cell, deducing genotypes of two chromosomes from a male parent and a female parent respectively by means of a maximum parsimony of recombination, to determine male parent a/female parent b typing results of the SNP site genotypes of the single cell; dividing a chromosome of the species into linkage regions based on the male parent a/female parent b typing results of the SNP site genotypes of the single cell, wherein a standard of dividing the chromosome of the species into linkage regions is that: (1) the SNP number comprising continuous same a or b is at least 5; (2) a physical length of a selected linkage region is greater than 250 kb; based on the determined linkage region, determining the haplotype of the single cell, wherein a set of a or b in the same linkage regions of the whole genome constituents the haplotype of the single cell. The method of determining the haplotype of the single cell of the present disclosure can be used to effectively determine the haplotype of the single cell derived from a mammal, particularly derived from human.

According to embodiments of the present disclosure, in the method of determining the haplotype of the single cell of the present disclosure, kinds of the species are not subjected to special restrictions, according to some specific examples of the present disclosure, the species is a mammal. According to other embodiments of the present disclosure, preferably, the mammal is human.

According to embodiments of the present disclosure, in the method of determining the haplotype of the single cell of the present disclosure, kinds of the single cell are not subjected to special restriction. According to some embodiments of the present disclosure, the single cell is a germ cell. According to some specific examples of the present disclosure, the single cell is a sperm cell.

According embodiments of the present disclosure, in the method of determining the haplotype of the single cell of the present disclosure, methods and platforms for the whole genome sequencing are not subjected to special restrictions, according to some specific examples of the present disclosure, the whole genome sequencing may be performed using a Next-Generation or a Third-Generation sequencing platform.

According embodiments of the present disclosure, in the method of determining the haplotype of the single cell of the present disclosure, the step of whole genome sequencing the single cell, to obtain a whole genome sequencing data of the single cell may further comprise: lysing the single cell to release a whole genome DNA using an alkaline lysis method; amplifying the whole genome DNA, to obtain an amplified whole genome DNA; for the amplified whole genome DNA, constructing a sequencing-library, to obtain a sequencing-library of the single cell; and sequencing the sequencing-library of the single cell, to obtain the every whole genome sequencing data of the at least one single cell.

According embodiments of the present disclosure, in the method of determining the haplotype of the single cell of the present disclosure, the single cell is a sperm cell, and the released whole genome DNA is subjected to a guanidine hydrochloride treatment after the single cell is lysed to release a whole genome DNA. According to some embodiments of the present disclosure, the guanidine hydrochloride treatment is performed using a solution of guanidine hydrochloride having a concentration of $2 \times 10^{-3}$ to $3 \times 10^{-1}$ mol/L. According to some specific examples of the present disclosure, the single cell derives from human, and the solution of guanidine hydrochloride having a concentration of $2 \times 10^{-3}$ mol/L.

According to embodiments of the present disclosure, in the method of determining the haplotype of the single cell of the present disclosure, the reference sequence is a known genomic sequence of the species.

According to embodiments of a fourth broad aspect of the present disclosure, there is provided a device of determining a haplotype of a single cell. According to embodiments of the present disclosure, the device may comprise: a single cell whole genome sequencing unit, for whole genome sequencing the single cell, to a whole genome sequencing data of the single cell; an SNP site genotype statistical unit, connected to the single cell whole genome sequencing unit, for aligning the obtained whole genome sequencing data to a reference sequence, to determine SNP site genotypes of the single cell; a parent typing unit, connected to the SNP site genotype statistical unit, for based on the SNP site genotypes of the single cell, deducing genotypes of two chromosomes from a male parent and a female parent respectively by means of a maximum parsimony of recombination, to determine male parent a/female parent b typing results of the SNP site genotypes of the single cell; a linkage region dividing unit, connected to the parent typing unit, for dividing a chromosome of the species into linkage regions based on the male parent a/female parent b typing results of the SNP site genotypes of the single cell, wherein a standard of dividing the chromosome of the species into linkage regions is that: (1) the SNP number comprising continuous same a or b is at least 5; (2) a physical length of a selected linkage region is greater than 250 kb; a haplotype determining unit, connected to the linkage region dividing unit, for based on the determined linkage region, determining the haplotype of the single cell, wherein a set of a or b in the same linkage regions of the whole genome constituents the haplotype of the single cell. The device of determining the haplotype of the single cell of the present disclosure can be used to effectively determine the haplotype of the single cell derived from a mammal, particularly derived from human.

According to embodiments of the present disclosure, in the device of determining the haplotype of the single cell of the present disclosure, the single cell whole genome sequencing unit may further comprise: a cellular whole genome DNA obtaining subunit, for lysing the single cell to release a whole genome DNA using an alkaline lysis method; a whole genome DNA amplifying subunit, connected to the cellular whole genome DNA obtaining subunit, for amplifying the whole genome DNA, to obtain an amplified whole genome DNA; and a whole genome DNA sequencing subunit, connected to the whole genome DNA amplifying subunit, for constructing a sequencing-library for the amplified whole genome DNA, to obtain a sequencing-library of the single cell, and sequencing the sequencing-library of the single cell, to obtain the every whole genome sequencing data of the at least one single cell.

According to embodiments of the present disclosure, in the device of determining the haplotype of the single cell of the present disclosure, the cellular whole genome DNA obtaining subunit is further suitable for subjecting the released whole genome DNA to a guanidine hydrochloride treatment after the single cell is lysed to release a whole genome DNA.

According to embodiments of the present disclosure, in the device of determining the haplotype of the single cell of the present disclosure, platforms can be used as the whole genome DNA sequencing subunit are not subjected special restrictions, according to some special examples of the present disclosure, the whole genome DNA sequencing subunit is suitable for using at least one of a Next-Generation and a Third-Generation sequencing platform.

It should be noted that the present disclosure uses a whole genome sequencing technology to obtain a single cell whole genome sequence data, which are subjected to analysis and process of bioinformatics by which can obtain a genetic map with high solution for haplotype analysis.

In details:

According to the embodiments of the present disclosure, the first aspect of the present disclosure relates to a method of constructing a genetic map based on a single cell, which may comprise following steps:

whole genome sequencing to obtain a whole genome sequence of a single cell derived from a same species;

aligning the obtained whole genome sequence to a reference sequence of the species, to obtain a genotype data comprising the single nucleotide polymorphism (SNP) of all single cell individuals;

based on the obtained genotype data, deducing genotypes of two chromosomes from a male parent and a female parent respectively by means of a maximum parsimony of recombination (MPR);

dividing a chromosome into linkage regions (LR, also known as bin) based on the typed SNP genotype result, in which a standard of dividing the chromosome into bins is that:

(1) the SNP number comprising continuous same SNP (i.e. both are a or b) is at least 5; (2) a physical length of a bin is greater than 250 kb;

after obtaining a bin type, calculating a variation ratio of a/b by subjecting bin information of all cells to statistical test, which may further obtain a recombination rate between every two continuous bins;

obtaining a recombination map based on the recombination rate between every two continuous bins; in which a boundary site between two bins of a type and b type respectively is a recombination site, obtaining a recombination rate of each recombination site by subjecting a plurality of samples to a statistical test to determine a recombination information at the recombination site; and obtaining a genetic map finally.

According to embodiments of the present disclosure, in the constructing method of first aspect of the present disclosure, the species is a higher animal having a limited progeny number, such as a mammal; according to some specific examples of the present disclosure, the species is human.

According to embodiments of the present disclosure, in the constructing method of first aspect of the present disclosure, the single cell may be a germ cell, according to some specific examples of the present disclosure, the single cell is a sperm cell.

According to embodiments of the present disclosure, in the constructing method of first aspect of the present disclosure, the method of obtaining the whole genome sequence of the single cell derived from a certain species is a conventional method known and used by those skilled in the art, in which comprises following steps of obtaining the whole genome DNA of the cell, amplifying the whole genome DNA and sequencing the whole DNA;

According to embodiments of the present disclosure, in the constructing method of first aspect of the present disclosure, the method of amplifying the whole genome DNA is a conventional method known and used by those skilled in the art, for example which may be degenerate oligonucleotide-primed PCR (DOP-PCR), ligation mediated PCR (LM-PCR), improved primer extension pre-amplification (I-PEP), multiple displacement amplification (MDA) or primase-based whole genome amplification (pWGA), and the like, according to some specific examples of the present disclosure, the method of amplifying the whole genome DNA is a strand displacement amplification based isothermal amplification method, such as MDA.

According to embodiments of the present disclosure, in the constructing method of first aspect of the present disclosure, a high-throughput sequencing method which is conventional in the art may be used for the whole genome sequencing, for example a Next-Generation sequencing technique represented by Illumina Solexa, ABI SOLiD and Roche 454, and a Third sequencing technique (i.e. a single molecule sequencing technique), such as real single molecule sequencing technology of Helicos company, single molecule real time sequencing technology of Pacific Biosciences company, nanopore sequencing technology of Oxford Nanopore Technologies company; according to an example of the present disclosure, Illumina Solexa of the Next-Generation sequencing technique is used.

According to embodiments of the present disclosure, in the constructing method of first aspect of the present disclosure, the step of obtaining the whole genome DNA of the cell may comprise a sub-step of using a trace of guanidine hydrochloride. According to an example of the present disclosure, the single cell is lysed using an alkaline lysis at room temperature to release the whole genome DNA, and then the released whole genome DNA is subjected to a guanidine hydrochloride treatment, in which the guanidine hydrochloride treatment is performed using a solution of guanidine hydrochloride having a final concentration of $2 \times 10^{-3}$ to $3 \times 10^{-1}$ mol/L, according to some specific examples of the present disclosure, the solution of guanidine hydrochloride having a final concentration of $2 \times 10^{-3}$ mol/L. According to some specific examples of the present disclosure, the single cell is a sperm cell.

According to embodiments of the present disclosure, in the constructing method of first aspect of the present disclosure, the method of aligning the obtained whole genome sequence to the reference sequence of the species to obtain the statistical result of SNP site genotype is a known and commonly-used method to those skilled in the art, according to some specific examples of the present disclosure, the method of aligning the obtained whole genome sequence to the reference sequence of the species to obtain the statistical result of SNP site genotype may comprise following steps:

establishing an index by taking a reference sequence (such as Hg19) of the species (such as human) as a control, aligning the whole genome sequence data obtained from sequencing to the index using a nucleic acid sequence aligning software (such as SOAP) to obtain the aligned result;

subjecting the aligned result to an SNP detecting software (such as SOAPsnp) to obtain a cns document of call SNP result, by taking a fasta document of the reference sequencing (such as Hg19) and dbSNP as controls;

screening the cns document to obtain a liable SNP site data by subjecting the cns document to further process;

integrating SNP site data derived from different single cells into one file, to obtain a statistical result comprising every SNP site genotype of all the single cells.

According to embodiments of the present disclosure, the second aspect of the disclosure relates to a device of constructing a genetic map based on single cell sequencing (FIG. 2), comprising:

a single cell whole genome sequencing unit, for obtaining a whole genome sequence derived from a single cell of a certain species;

an SNP site genotype statistical unit, connected to the single cell whole genome sequencing unit, for aligning the whole genome sequence derived from the single cell of the certain species to a reference sequence of the certain species, to obtain a statistical result of SNP site genotypes;

a parent typing unit, connected to the SNP site genotype statistical unit, for deducing genotypes of two chromosomes from a male parent and a female parent respectively by means of a maximum parsimony of recombination based on the every SNP site genotypes of the at least one single cell, to determine male parent a/female parent b typing results of every SNP genotype of the at least one single cell;

a linkage region (bin) dividing unit, connected to the parent typing unit, for dividing a chromosome of the species into linkage regions (bins) based on the male parent a/female parent b typing results of every SNP genotype of the at least one single cell, wherein a standard of dividing the chromosome of the species into linkage regions is that: (1) the SNP number comprising continuous same a or b is at least 5; (2) a physical length of a selected linkage region is greater than 250 kb;

a recombination rate between contiguous linkage regions calculating unit, connected to the linkage region dividing unit, for calculating a variation ratio of a/b between two every two continuous bins, to obtain a recombination rate between every two continuous bins after obtaining the type of bin, and based on the recombination rate between every two continuous bins, determining a recombination map, in which a boundary site between a and b is a recombination site;

a recombination rate of the recombination site calculating unit, for determining a recombination rate of each recombination site, to construct the genetic map of the species based on recombination maps of all single cells by subjecting the recombination information of the plurality of samples to a statistical test.

According to embodiments of the present disclosure, in the device of constructing the genetic map of the second aspect of the present disclosure, the species is a higher animal having a limited progeny number, such as a mammal; according to some specific examples of the present disclosure, the species is human.

According to embodiments of the present disclosure, in the device of constructing the genetic map of the second aspect of the present disclosure, the single cell may be a germ cell, according to some specific examples of the present disclosure, the single cell is a sperm cell.

According to embodiments of the present disclosure, in the device of constructing the genetic map of the second aspect of the present disclosure, the single cell whole genome sequencing unit further comprises: a cellular whole genome DNA obtaining subunit, a whole genome DNA amplifying subunit, and a whole genome DNA sequencing subunit.

According to embodiments of the present disclosure, in the device of constructing the genetic map of the second aspect of the present disclosure, the cellular whole genome DNA obtaining subunit is used for obtaining the whole genome DNA of the single cell, in which the step of obtaining the whole genome DNA of the cell comprises a sub-step of using a trace of guanidine hydrochloride. According some embodiments of the present disclosure, the single cell is lysed using an alkaline lysis at room temperature to release the whole genome DNA, and then the released whole genome DNA is subjected to a guanidine hydrochloride treatment, in which the guanidine hydrochloride treatment is performed using a solution of guanidine hydrochloride having a final concentration of $2\times10^{-3}$ to $3\times10^{-1}$ mol/L, according to some specific examples of the present disclosure, the solution of guanidine hydrochloride having a final concentration of $2\times10^{-3}$ mol/L. According to some embodiments of the present disclosure, the single cell is a sperm cell.

According to embodiments of the present disclosure, in the device of constructing the genetic map of the second aspect of the present disclosure, the whole genome DNA amplifying subunit is used for amplifying the obtained whole genome DNA, in which the method of amplifying the whole genome DNA, for example, may be DOP-PCR, LM-PCR, I-PEP, MDA or pWGA and the like, according to some specific examples of the present disclosure, the method of amplifying the whole genome DNA is a strand displacement amplification based isothermal amplification method, such as MDA.

According to embodiments of the present disclosure, in the device of constructing the genetic map of the second aspect of the present disclosure, the whole genome DNA sequencing subunit is used for amplifying the obtained whole genome DNA, in which the method of sequencing the whole genome DNA, for example, may be a Next-Generation sequencing technique represented by Illumina Solexa, ABI SOLiD and Roche 454, and a Third sequencing technique (i.e. a single molecule sequencing technique), such as real single molecule sequencing technology of Helicos company, single molecule real time sequencing technology of Pacific Biosciences company, nanopore sequencing technology of Oxford Nanopore Technologies company; according to an example of the present disclosure, Illumina Solexa of the Next-Generation sequencing technique is used.

According to embodiments of the present disclosure, in the device of constructing the genetic map of the second aspect of the present disclosure, the SNP site genotype statistical unit is used for aligning the obtained whole genome sequence to a reference sequence of the species, to obtain a statistical result of the SNP site genotype, in which the used method is known and commonly-used methods to those skilled in the art, according to some specific examples of the present disclosure, the method of obtaining the statistical result of the SNP site genotype comprises following modules:

aligning module: used for establishing an index by taking a reference sequence (such as Hg19) of the species (such as human) as a control, aligning the whole genome sequence data obtained from sequencing to the index using a nucleic acid sequence aligning software (such as SOAP) to obtain the aligned result;

a detecting module: used for subjecting the obtain the aligned result to an SNP detecting software (such as SOAPsnp) to obtain a cns document of call SNP result, by taking a fasta document of the reference sequencing (such as Hg19) and dbSNP as controls;

a screening module: used for screening the cns document to obtain a liable SNP site data by subjecting the cns document to further process;

an integrating module: used for integrating SNP site data derived from different single cells into one file, to obtain a statistical result comprising every SNP site genotype of all the single cells.

According to embodiments of the present disclosure, the third aspect of the present disclosure relates to a method of determining a haplotype of a single cell, which comprises following steps:

whole genome sequencing the single cell, to obtain a whole genome sequencing data of the single cell of a certain species;

aligning the obtained whole genome sequencing data to a reference sequence, to determine genotype data of single nucleotide polymorphism (SNP) of the single cell;

based on the obtained genotype data, by means of a maximum parsimony of recombination, deducing genotypes of two chromosomes from a male parent and a female parent respectively in the case of minimal recombination events, to determine male parent a/female parent b typing results of the SNP site genotypes of the single cell;

based on the male parent a/female parent b typing results of the SNP site genotypes of the single cell, dividing a chromosome into bins, wherein a standard of dividing the chromosome of into bins is that: (1) the SNP number comprising continuous same a or b is at least 5; (2) a physical length of a selected linkage region is greater than 250 kb;

determining the haplotype of the single cell based on the determined bin, i.e. a set of a or b in the same bin of the whole genome is the haplotype of the single cell.

According to embodiments of the present disclosure, in the method of determining the haplotype of the single cell of the third aspect of the present disclosure, the species is a higher animal having a limited progeny number, such as a mammal; according to some specific examples of the present disclosure, the species is human.

According to embodiments of the present disclosure, in the method of determining the haplotype of the single cell of the third aspect of the present disclosure, the single cell may be a germ cell, according to some specific examples of the present disclosure, the single cell is a sperm cell.

According to embodiments of the present disclosure, in the method of determining the haplotype of the single cell of the third aspect of the present disclosure, the method of obtaining the whole genome sequence of the single cell derived from a certain species is a conventional method known and used by those skilled in the art, in which comprises steps of obtaining the whole genome DNA of the cell, amplifying the whole genome DNA and sequencing the whole DNA;

According to embodiments of the present disclosure, in the method of determining the haplotype of the single cell of the third aspect of the present disclosure, the method of amplifying the whole genome DNA, for example, may be DOP-PCR, LM-PCR, I-PEP, MDA or pWGA and the like, according to some specific examples of the present disclosure, the method of amplifying the whole genome DNA is a strand displacement amplification based isothermal amplification method, such as MDA.

According to embodiments of the third aspect of the present disclosure, in the method of determining the haplotype of the single cell of the present disclosure, the method of sequencing the whole genome DNA, for example, may be a Next-Generation sequencing technique represented by Illumina Solexa, ABI SOLiD and Roche 454, and a Third sequencing technique (i.e. a single molecule sequencing technique), such as real single molecule sequencing technology of Helicos company, single molecule real time sequencing technology of Pacific Biosciences company, nanopore sequencing technology of Oxford Nanopore Technologies company; according to an example of the present disclosure, Illumina Solexa of the Next-Generation sequencing technique is used.

According to embodiments of the third aspect of the present disclosure, in the method of determining the haplotype of the single cell of the third aspect of the present disclosure, the step of obtaining the whole genome DNA of the cell comprises a sub-step of using a trace of guanidine hydrochloride. According some embodiments of the present disclosure, the single cell is lysed using an alkaline lysis at room temperature to release the whole genome DNA, and then the released whole genome DNA is subjected to a guanidine hydrochloride treatment, in which the guanidine hydrochloride treatment is performed using a solution of guanidine hydrochloride having a final concentration of $2 \times 10^{-3}$ to $3 \times 10^{-1}$ mol/L, according to some specific examples of the present disclosure, the solution of guanidine hydrochloride having a final concentration of $2 \times 10^{-3}$ mol/L. According to some embodiments of the present disclosure, the single cell is a sperm cell.

According to embodiments of the third aspect of the present disclosure, in the method of determining the haplotype of the single cell of the third aspect of the present disclosure, the method of aligning the obtained whole genome sequence to the reference sequence of the species to obtain the statistical result of SNP site genotype is a known and commonly-used method to those skilled in the art, according to some specific examples of the present disclosure, the method of aligning the obtained whole genome sequence to the reference sequence of the species to obtain the statistical result of SNP site genotype may comprise following steps:

establishing an index by taking a reference sequence (such as Hg19) of the species (such as human) as a control, aligning the whole genome sequence data obtained from sequencing to the index using a nucleic acid sequence aligning software (such as SOAP) to obtain the aligned result;

subjecting the aligned result to an SNP detecting software (such as SOAPsnp) to obtain a cns document of call SNP result, by taking a fasta document of the reference sequencing (such as Hg19) and dbSNP as controls;

screening the cns document to obtain a liable SNP site data by subjecting the cns document to further process;

integrating SNP site data derived from different single cells into one file, to obtain a statistical result comprising every SNP site genotype of all the single cells.

According to embodiments of the present disclosure, the fourth aspect of the present disclosure relates to a device of determining a haplotype of a single cell (FIG. 3), which comprises:

a single cell whole genome sequencing unit, for obtaining a whole genome sequence of the single cell derived from a certain species;

an SNP site genotype statistical unit, connected to the single cell whole genome sequencing unit, for aligning the obtained whole genome sequencing data to a reference sequence, to obtain a statistical result of SNP site genotype;

a parent typing unit, connected to the SNP site genotype statistical unit, for deducing genotypes of two chromosomes from a male parent and a female parent respectively by means of a maximum parsimony of recombination based on the SNP site genotypes of the single cell, to determine male parent a/female parent b typing results of the SNP site genotypes of the single cell;

a linkage region (bin) dividing unit, connected to the parent typing unit, connected to the parent typing unit, for dividing a chromosome of the species into linkage regions (bin) based on the male parent a/female parent b typing results of the SNP site genotypes of the single cell, wherein a standard of dividing the chromosome of the species into linkage regions is that: (1) the SNP number comprising continuous same a or b is at least 5; (2) a physical length of a selected bin is greater than 250 kb;

a haplotype determining unit, connected to the linkage region (bin) dividing unit, for determining the haplotype of the single cell based on the determined linkage region (bin), wherein a set of a or b in the same linkage regions (bins) of the whole genome constituents the haplotype of the single cell.

According to embodiments of the present disclosure, in the device of determining he haplotype of the single cell of the fourth aspect of the present disclosure, the species is a higher animal having a limited progeny number, such as a mammal; according to some specific examples of the present disclosure, the species is human.

According to embodiments of the present disclosure, in the device of determining he haplotype of the single cell of the fourth aspect of the present disclosure, the single cell may be a germ cell, according to some specific examples of the present disclosure, the single cell is a sperm cell.

According to embodiments of the present disclosure, in the device of determining he haplotype of the single cell of the fourth aspect of the present disclosure, the single cell whole genome sequence unit comprises a cellular whole genome DNA obtaining subunit, a whole genome DNA amplifying subunit, and a whole genome DNA sequencing subunit.

According to embodiments of the present disclosure, in the device of determining he haplotype of the single cell of the fourth aspect of the present disclosure, the cellular whole genome DNA obtaining subunit is used for obtaining the cellular whole genome DNA, the step of obtaining the whole genome DNA of the cell may comprise a sub-step of using a trace of guanidine hydrochloride. According to an example of the present disclosure, the single cell is lysed using an alkaline lysis at room temperature to release the whole genome DNA, and then the released whole genome DNA is subjected to a guanidine hydrochloride treatment, in which the guanidine hydrochloride treatment is performed using a solution of guanidine hydrochloride having a final concentration of $2\times10^{-3}$ to $3\times10^{-1}$ mol/L, according to some specific examples of the present disclosure, the solution of guanidine hydrochloride having a final concentration of $2\times10^{-3}$ mol/L. According to some specific examples of the present disclosure, the single cell is a sperm cell.

According to embodiments of the present disclosure, in the device of determining he haplotype of the single cell of the fourth aspect of the present disclosure, the whole genome DNA amplifying subunit is used for amplifying the obtained cellular whole genome DNA, the method of amplifying the whole genome DNA, for example, may be DOP-PCR, LM-PCR, I-PEP, MDA or pWGA and the like, according to some specific examples of the present disclosure, the method of amplifying the whole genome DNA is a strand displacement amplification based isothermal amplification method, such as MDA.

According to embodiments of the present disclosure, in the device of determining he haplotype of the single cell of the fourth aspect of the present disclosure, the whole genome DNA sequencing subunit is used for sequencing the amplified whole genome DNA, the method of sequencing the whole genome DNA, for example, may be a Next-Generation sequencing technique represented by Illumina Solexa, ABI SOLiD and Roche 454, and a Third sequencing technique (i.e. a single molecule sequencing technique), such as real single molecule sequencing technology of Helicos company, single molecule real time sequencing technology of Pacific Biosciences company, nanopore sequencing technology of Oxford Nanopore Technologies company; according to an example of the present disclosure, Illumina Solexa of the Next-Generation sequencing technique is used.

According to embodiments of the present disclosure, in the device of determining he haplotype of the single cell of the fourth aspect of the present disclosure, the SNP site genotype statistical unit is used for aligning the whole genome sequence to a reference sequence of the certain species, to obtain a statistical result of SNP site genotypes, the used method is known and commonly-used methods to those skilled in the art, according to some specific examples of the present disclosure, the method of obtaining the statistical result of the SNP site genotype comprises following modules:

aligning module: used for establishing an index by taking a reference sequence (such as Hg19) of the species (such as human) as a control, aligning the whole genome sequence data obtained from sequencing to the index using a nucleic acid sequence aligning software (such as SOAP) to obtain the aligned result;

a detecting module: used for subjecting the obtain the aligned result to an SNP detecting software (such as SOAPsnp) to obtain a cns document of call SNP result, by taking a fasta document of the reference sequencing (such as Hg19) and dbSNP as controls;

a screening module: used for screening the cns document to obtain a liable SNP site data by subjecting the cns document to further process;

an integrating module: used for integrating SNP site data derived from different single cells into one file, to obtain a statistical result comprising every SNP site genotype of all the single cells.

According to embodiments of the present disclosure, the fifth aspect of the present disclosure relates to a method of extracting a whole genome DNA from a cell, which comprises a step of using a trace of guanidine hydrochloride after lysing the cell, a solution of guanidine hydrochloride having a final concentration of $2\times10^{-3}$ to $3\times10^{-1}$ mol/L, according to some specific examples of the present disclosure, the solution of guanidine hydrochloride having a final concentration of $2\times10^{-3}$ mol/L.

According to some specific examples of the present disclosure, the method of extracting the whole genome DNA from the cell comprises: lysing the single cell using an alkaline lysis to release the whole genome DNA, and then the released whole genome DNA is subjected to a guanidine hydrochloride treatment, in which the guanidine hydrochloride treatment is performed using a solution of guanidine hydrochloride having a final concentration of $2\times10^{-3}$ to $3\times10^{-1}$ mol/L, according to some specific examples of the present disclosure, the solution of guanidine hydrochloride having a final concentration of $2\times10^{-3}$ mol/L.

According to some specific examples of the present disclosure, the single cell is a sperm cell.

It should be noted that in the present disclosure, a role of the guanidine hydrochloride treatment is to denature a DNA binding protein, which may be used in extracting a whole genome from an ordinary cell. Due to a protamine of the sperm cell is difficult to remove, which will affect a coverage and a depth of subsequent sequencing, the method of the present disclosure is particularly suitable for extracting the whole genome DNA form the sperm cell.

The present disclosure also relates usage of the method of extracting the whole genome DNA from the cell of the fifth aspect of the present disclosure in sequencing a cell whole genome. According to some specific examples of the present disclosure, the cell is a sperm cell.

In addition, it should be also note that the present disclosure has following advantages, by whole genome sequencing the single cell and data analysis:

1) due to the mammal lacks a plenty of progenies for constructing a map, the method of selecting a germ cell having a haploid to construct a genetic map in the present disclosure overcomes a malpractice in material drawing of the traditional method, and the method of sampling thereof conforms to the statistical principle;

2) due to a precedent of performing genotype using the germ cell having the haploid has a limitation in research scope and technique, the present disclosure using the whole genome amplification, high-throughput sequencing combined with SNP typing may well solve this problem, which is able to cover all known genes and unknown region, and can detect maximal SNP genotypes in sequencing data, as well as obtain a genetic map with a highest resolution;

3) the method of the present disclosure may obtain a genetic map with a highest resolution by using a bioinformatics method to obtain a data information of the whole genome DNA and repeatedly probing the method of analyzing data;

4) the method constructing the genetic map may apply to human genetics, which may play an important role in genomics and genetics; and the suitable sample not only derives from human, the method is also suitable for various organisms most of which has a relative low fertility, particularly an endangered species. The method may be used to directly understand the genetic rules of fertility thereof which may guide the proliferation in accordance with the most preferred solution.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
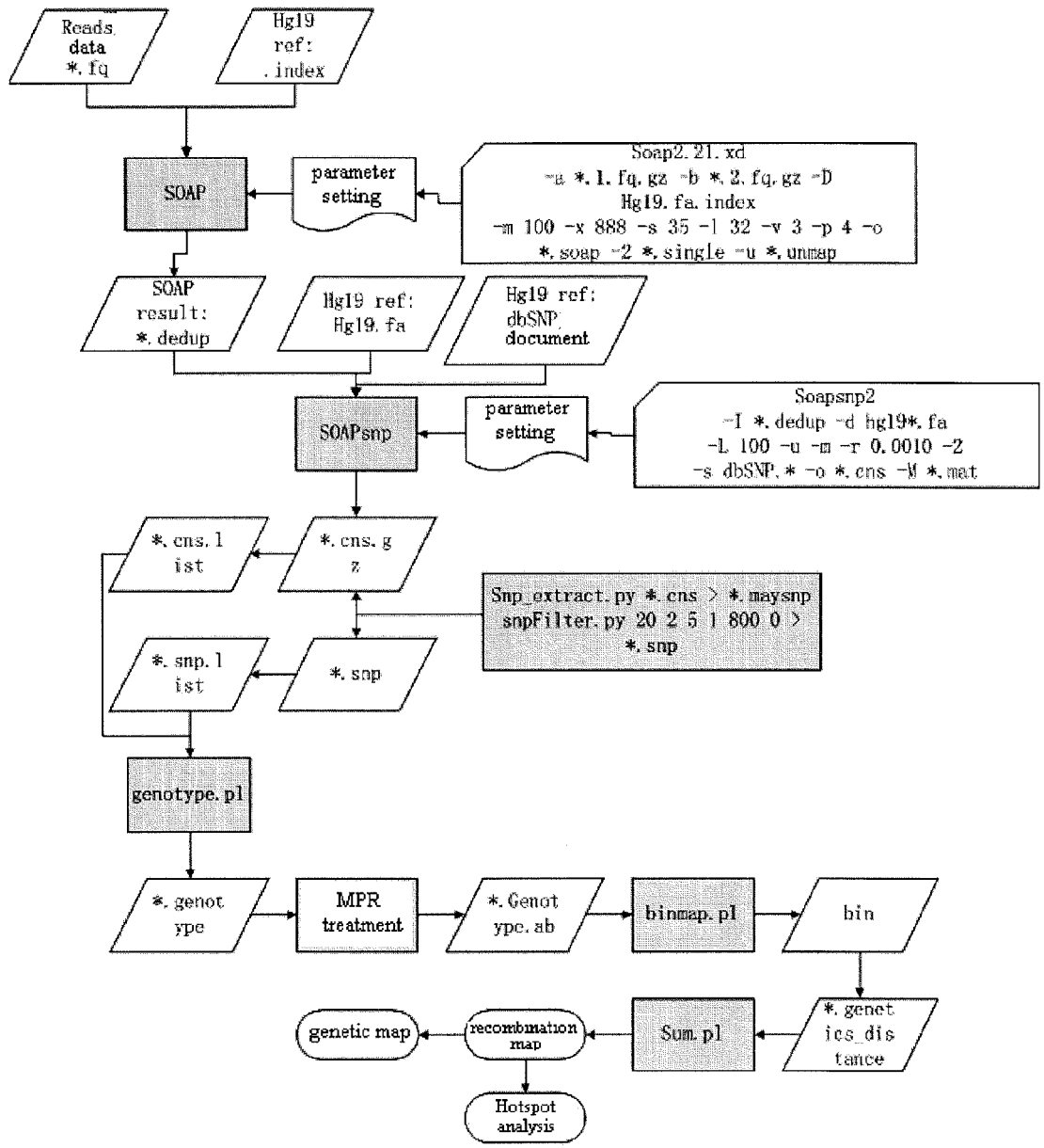
FIG. 1 is a flow chart of analyzing information of a genetic map constructed by a single sperm cell sequencing.
Figure 2:
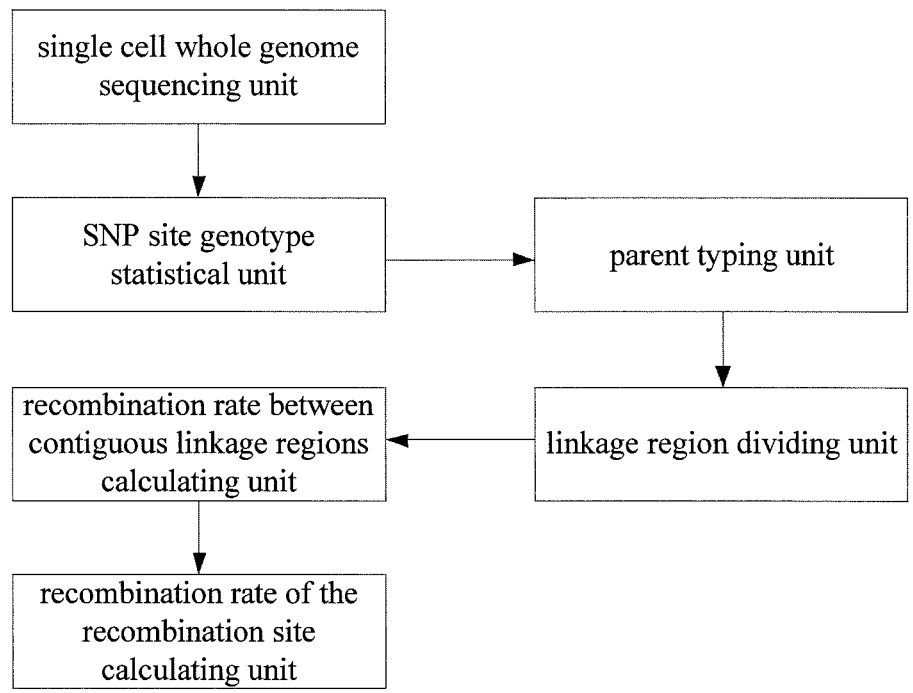
FIG. 2 is a device of constructing a genetic map according to an embodiment of the present disclosure.
Figure 3:
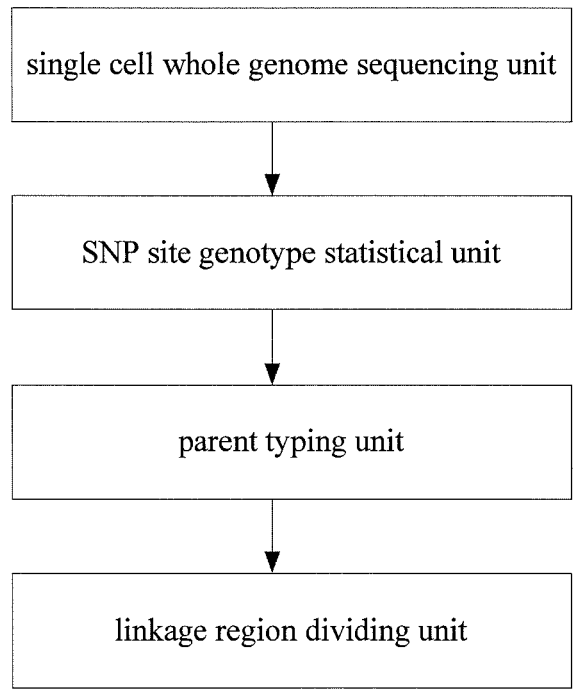
FIG. 3 is a device of determining a haplotype of a single cell according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

Based on the existing problem of constructing a genetic map of the single sperm in the prior art, the present disclosure provides a method of constructing a genetic map of a single sperm cell determining a haplotype thereof by combining single cell whole genome amplification, whole genome re-sequencing and genotyping. The method comprises an experimental process and an information analysis process, in which the experimental process is based on a single cell manipulation technique, specifically, based on an amplification technique of trace DNA isolated from a single cell to produce enough DNA sample from the single cell; the information analysis process is based on re-sequencing principle to obtain a genotype. Then according to a method of maximum parsimony of recombination, the whole genome of the single cell is subjected to a parents typing, to construct the genetic map finally.

According to embodiments of the present disclosure, a selection problem with the human family (it is difficult to select a large family to meet a requirement of a large number of individuals for constructing a genetic map) can be well solved by taking a human sperm cell as a drawn object, which may not only ensure the randomness of sampling but also solve the problem of sample population. The principle of taking each sperm cell as one progeny is also based on a genetic recombination occurred in meiosis, which is theoretically scientific and feasible; secondly, in order to remove the binding protein in the chromosome, particularly the protamine, to better release DNA, the sperm cell is lysed using an alkaline lysis at room temperature and then added with a trace of guanidine compound, such as GuHCl, to obtain a template for amplification with a high quality; finally, the obtained whole genome DNA of the sperm cell is subjected to whole genome sequencing by multiple displacement amplification (MDA) combined with a high-throughput whole genome sequencing technique, to realize analyzing the whole genome, which not only covers known genes but also cover all unknown regions, therefore a genetic map with a high resolution may be obtained.

The present disclosure are divided into two parts: experimental part and information part, in which the experimental part comprises: isolation of single sperm cell, cell lysis, multiple displacement amplification, quality control, library construction, sequencing, the aim thereof is to amplify the genome of the single sperm cell, and then to perform subsequent information analysis; the information part is divided into genotype analysis, genetic map construction and haplotype analysis.

In the present disclosure, after amplifying the whole genome, the method also comprises a step of subjecting the amplified product to a quality control, in which the step comprises:

a concentration of the amplified product: the amplified product of which the concentration achieves a certain standard is regarded as the qualified;

detection of coverage of the housekeeping gene: the amplified product is subjected to a detection as a housekeeping gene, when there are 70% or more of the housekeeping gene can be obtained by amplification in the sample, for example a target band man be seen during electrophoresis, then the amplified product can be subjected to further library construction and sequencing on computer.

In the present disclosure, the whole genome sequencing may be performed by conventional high-throughput sequencing method in the art, for example a Next-Generation sequencing technique represented by Illumina Solexa, ABI SOLiD and Roche 454, and a Third sequencing technique (i.e. a single molecule sequencing technique), such as real single molecule sequencing technology of Helicos company, single molecule real time sequencing technology of Pacific Biosciences company, nanopore sequencing technology of Oxford Nanopore Technologies company; according to an example of the present disclosure, Illumina Solexa of the Next-Generation sequencing technique is used.

According to some specific examples of the present disclosure, the method comprises an experimental manipulation process and an information analysis process:

1) Experimental Manipulation Process

A sample is purified by density gradient centrifugation, a single sperm cell is isolated from cell suspension under inverted microscope or by means of microfluidic; the single sperm cell is lysed to release chromosome DNA; the obtained DNA is subjected to denaturing treatment and then to multiple displacement amplification (MDA); the amplified genome DNA is subjected to quantification test; the concentration-qualified DNA sample is then subjected to PCR detection, by selecting a housekeeping gene in different chromosomes as a target fragment for PCR amplification and verifying the existence of the target band during electrophoresis. The sample which is qualified in the PCR detection may be then used in subsequent library construction and sequencing analysis, or in other genetics analysis. A period of preparing a DNA sample of a single cell is 3 to 4 days.

2) Information Analysis Process

See to FIG. 1.

a) establishing an index by taking a human Hg19 as a control, aligning the off-computer data obtained by sequencing to the index using a SOAP software (software version: SOAPaligner v2.21 http://soap.genomics.org.cn/), to obtain an aligned result.

b) taking a fasta document of the human Hg19 and Hg19 dbSNP as a reference, detecting the aligned result by SOAPsnp, to obtain a cns document of call SNP result.

c) screening the cns document to obtain a set of liable SNP sites.

d) integrating the SNP result of different single cells into one file, to obtain a statistical result of every SNP site genotype of all single cells.

e) deducing genotypes of two chromosomes from a male parent and a female parent respectively in the case of minimal recombination events by means of a maximum parsimony of recombination (maximum parsimony of recombination, Parent-independent genotyping for constructing an ultrahigh-density linkage map based on population sequencing. PNAS, 2010, 107, 10578-10583), to determine male parent a/female parent b typing results of every single cell;

f) dividing every SNP genotype result after into linkage regions (bins) in accordance with two standards: 1) the SNP number comprising continuous same a or b is at least 5; (2) a physical length of a selected bin is greater than 250 kb.

g) calculating a recombination rate by subjecting the recombination information between every two continuous bins to a statistical test, because a position range of each bin is known, a specific recombination information between every two continuous bins in every chromosome may be obtained.

h) finally a recombination map may be obtained according to different male parent a/female parent b typing result represented by different colors (a blank represents a genomic deletion region).

i) according to breakpoint information (color switching point) of the recombination map, making a slitting line at each breakpoint, subjecting all obtained non-repetitive tangent points to a statistical test of recombination number, which may obtain a genetic map.

j) for studying hot spot region of recombination, extracting relevant sequence and gene back in gff annovation document of Hg19, which may obtain more elaboration regarding some genes closely related to recombination, so as to verify the scientificity and feasibility of the solution of the present disclosure.

k) for haplotype blocks obtained by studying closely linked genetic region, probing some genetic characteristics of the closely linked genetic region.

The present disclosure demonstrates that a model of single cell sequencing may be applied to study human genetics, in which the model may play an important role in individual genomics and genetics, for all higher organisms (limited capacity of reproduction), such technique may be effectively applied, particularly some endangered species, which may guide and help the proliferation in accordance with the most preferred solution.

It should be noted that, the method and device of constructing the genetic map according to embodiments of the present disclosure, and the method and device of determining the haplotype of the single cell are completed through painstaking creative work and optimization effort by inventors of the present disclosure.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al. (translated by Huang PT), *Molecular Cloning: A Laboratory Manual*, 3rd Ed., Science Press) or in accordance with the product instructions. If the manufacturers of reagents or instruments are not specified, the reagents or instruments may be commercially available, for example, from Illumina company.

EXAMPLE 1

Recombination Map and Genetic Map Construction by Single Sperm Cell Sequencing 1.1 List of Reagent and Apparatus

TABLE 1

| Reagents stored at −20° C. | | |
| --- | --- | --- |
| Name | manufacturer | Art. No. |
| REPLI-g Mini Kit | Qiagen | 150025 |
| 100X BSA | NEB | |
| dNTP | NEB | |
| rTaq DNA polymerase | Takara | |

TABLE 2

| Reagents stored at 4° C. | | |
| --- | --- | --- |
| Name | Manufacturer | Art. No. |
| Nuclease free water | Promega | |
| PureCeption ™ 4-Determination Kit | CooperSurgical | ART-2004 |
| Sperm Washing Medium | CooperSurgical | ART-1005 |

TABLE 3

| Reagents stored at room temperature (RT) | | |
| --- | --- | --- |
| Name | Manufacturer | Art. No. |
| Quant-iT ™ buffer | Invitrogen | |
| Quant-iT ™ reagent | Invitrogen | |

TABLE 4 commonly-used consumable and apparatus

| Name | Manufacturer |
| --- | --- |
| 0.2 mL PCR tube | Axygen |
| 1.5 mL centrifuge tube | Axygen |
| 2 mL centrifuge tube | Axygen |
| 0.1-10 μL tip | Axygen |
| 2-200 μL tip | Axygen |
| 5-1000 μL tip | Axygen |
| 96-well PCR plate | Axygen |
| Mouth-controlled pipette | Domestic |
| Centrifuge | Eppendorf |
| Qubit | Invitrogen |
| Gel Imaging System | Tanon |

1×PBS solution was prepared by:
weighing following reagents into a beaker having a volume of 1 liter, and
adding 800 mL deionized water,

| | |
| --- | --- |
| NaCl | 8 g |
| KCl | 0.2 g |
| $Na_2HPO_4$ | 1.44 g |
| $KH_2PO_4$ | 0.23 g | adjusting pH to a value of 7.4, and adding the deionized water up to 1 L,
autoclaving at a high temperature and high pressure,
storing at 4V.

The prepared 1×PBS solution was added with 15 mg/ml BSA when being used.

ALB solution was prepared by:
weighing 0.02244 g KOH solid into a centrifuge tube having a volume of 2 mL,
adding 2 mL ultrapure water and 101 μL DTT solution (1M),
mixing by up and down.

The prepared ALB solution was filtered using a filter having an aperture of 0.2 μm inside an ultra-clean bench. The filtered solution was then stored at 4° C. immediately, which could be kept for one week.

1.2 Sampling and Isolating of the Single Cell

See to reference (Specific and complete human genome amplification with improved yield achieved by phi29 DNA polymerase and a novel primer at elevated temperature. *BMC Res Notes.* 2009, 2, 48-48. Whole genome amplification: abundant supplies of DNA from precious samples or clinical specimens. *Trends Biotechnol.* 2003, 21(12): 531-535.).

Sample resource: Guangdong Key Laboratory of male reproductive and genetics, Peking University Shenzhen Hospital Sperm resource: a healthy male without any illness, 54 years old, and children bearing whose sperm had a density of $92.5×10^6$/mL, and an activity of 8.7%.

1.2.1 Sample Pretreating Due to the sampled seminal fluid was relative viscous, the single cells were firstly subjected to removing impurities, and were uniformly dispersed in liquid phase which was available for operating.

a) if a sample of seminal fluid was relative viscous, the sample was firstly subjected to liquefaction by being placed at 37° C. for 30 min.

b) PureCeption and washing buffer were taken out from 4° C. shelf for use.

c) One freezing tube having a volume of 2 mL was used for preparing a gradient centrifugation purification column, which was firstly added with 600 μL PureCeption 80%, and then slowly added with 600 μL PureCeption 40% on the top of liquid, by which a layered interface was obaserved.

d) 600 μL liquefied seminal fluid was slowly added to the stratosphere of the purification column, and then centrifuged at 350 g~400 g for 20 minutes.

e) After the upper layer was removed, only about 100 μL of most bottom layer was conserved. After being added with 600 μL of the washing buffer, and then centrifuged at 250 g for 4~8 minutes.

f) After the upper layer was removed, 100 μL of the washing buffer was added. Then the obtained mixture was used in single cell isolation.

1.2.2 Single Cell Isolation

The single cell could be isolated by a method of mouth-controlled pipette or microfluidic, and be conserved.

a) 3 droplets of 1×PBS large droplets (each had a volume of 20 μL) were added into a clean dish for conserve cell suspension. For each cell sample, an array of 1×PBS small droplets having a volume of 3 μL were made. Droplets of mineral oil were added to cover all the above droplets.

b) 1~2 μL of cell suspension was transferred into the 1×PBS large droplet in the dish by a mouth-controlled pipette. All operations using the mouth-controlled pipette should be performed under a microscope to ensure the suspension entering into the 1×PBS large droplet, other than the droplet of mineral oil.

c) a few of cells were transferred from the 1×PBS large droplet to the 1×PBS small droplet using the mouth-controlled pipette, while such operation of the cell entering into the 1×PBS small droplet was observed under the microscope.

d) then a selected cell was transferred from one 1×PBS small droplet into another by the mouth-controlled pipette, by which each cell was isolated and washed gradually. Finally, single cell of each suction could be obtained.

e) the finally obtained single cell were transferred into a PCR tube containing 1.5 μL of ALB solution, along with no more than 2 μL of added 1×PBS. Each tube only contained one single cell was confirmed by microscope.

f) the obtained single cell was frozen at −20° C. or −80° C. for at least 30 min, but no more than one week.

1.3 Multiple Displacement Amplification (MDA)

In prior art, how to guarantee the amplification in the process of the single sperm cell whole genome amplification was one key point; when amplifying DNA obtained from lysing the single sperm cell, phenomenons of low coverage and high bias appeared, which was due to DNA binding protein (mainly protamine) in chromosome of the single sperm cell would result to a highly-concentrated genome; however the protamine was hard to remobe, thus a method which could both analyzing the whole genome sequence and solving the problems of low coverage and high bias was needed.

Although a prior study used a treatment of 6~8 mol/L GuHCl to denature the protamine, a most optimal working concentration under a condition of single cell amplification had not been evaluated (Bienvenue, J. M., N. Duncalf, et al. (2006). "Microchip-based cell lysis and DNA extraction from sperm cells for application to forensic analysis." *J Forensic Sci* 51(2): 266-73.). Considering a strong reducing property of 6~8 mol/L GuHCl could easy destroy an activity of Phi29 DNA polymerase under a condition of microreaction, the present disclosure set 4 different gradients of GuHCL: $8×10^{-1}$ mol/L, $8×10^{-2}$ mol/L, $8×10^{-3}$ mol/L [final concentrations correspondingly were respectively $(2~3)×10^{-1}$ mol/L, $(2~3)×10^{-2}$ mol/L, $(2~3)×10^{-3}$ mol/L] and 0, finally after quantifying the obtained product, comparing the coverage of housekeeping gene and whole genome, a most optimal treating concentration of $8×10^{-3}$M in amplification of human single sperm whole genome was determined (specific experimental results were shown in Table 5).

The single cell was lysed using an alkaline lysis at room temperature to release the chromosomal DNA, and then the released chromosomal DNA was subjected to a GuHCl treatment, in which the GuHCl treatment was performed using a solution of GuHCl having a concentration of $8\times10^{-3}$ mol/L, the GuHCl-treated chromosomal DNA was then subjected to denaturing by buffer D1, buffer N1 (both buffer D1 and buffer N1 were from REPLI-g Mini kit, Qiagen), and then the denatured chromosomal DNA was subjected MDA amplification, the process of amplification was performed referring to Whole-genome multiple displacement amplification from single cells, *Nature Protocols* 2006, 1, 1965-1970.

1.4 Quality Control of the MDA Amplification Product

The quality control of the MDA amplification product was performed referring to instruction of Invitrogen (Quant-iT™ Assays Qubit Abbreviated Protocol for the Qubit Fluorometer), which comprises following two steps: the MDA amplified product of which the concentration achieves a certain standard was regarded as the qualified; Detection of MDA amplification effect using housekeeping gene: a qualified sample assayed by Qubit concentration quantification was selected as a housekeeping gene for coverage detection; after being diluted using $ddH_2O$, the amplified sample was added with a primer and Taq enzyme to perform PCR amplification. The obtained product of housekeeping gene was detected by electrophoresis. If there are 70% housekeeping genes of the

TABLE 5

The evaluation of the most optimal denaturing concention by GuHCl

| Sample Name | Conc. of GuHCl (mol/L) | Conc. of product (ng/µL) | Dection of coverage of housekeeping gene | Sequencing coverage Chr1 | Sequencing coverage Chr12 | Sequencing depth Chr1 | Sequencing depth Chr12 |
|---|---|---|---|---|---|---|---|
| S1-1 | $8\times10^{-1}$ | 97.1 | 8/10 | — | — | — | — |
| S1-2 | $8\times10^{-1}$ | 78.4 | 9/10 | — | — | — | — |
| S1-3 | $8\times10^{-1}$ | 103 | 9/10 | 27.78% | 31.19% | 1.99 | 2.3 |
| S2-1 | $8\times10^{-2}$ | 114 | 9/10 | — | — | — | — |
| S2-2 | $8\times10^{-2}$ | 89.5 | 6/10 | — | — | — | — |
| S3-1 | $8\times10^{-3}$ | 94.5 | 9/10 | — | — | — | — |
| S3-2 | $8\times10^{-3}$ | 89.4 | 8/10 | — | — | — | — |
| S3-3 | $8\times10^{-3}$ | 97.4 | 10/10 | 60.06% | 49.44% | 3.23 | 1.98 |
| S4-1 | 0 | 112 | 5/10 | — | — | — | — |
| S4-2 | 0 | 81.8 | 5/10 | — | — | — | — |

As can be seen from the above results, when the added solution of GuHCl having a concentration of $8\times10^{-3}$ mol/L, the obtained product had a best sequencing coverage and a best sequencing depth, thus the solution of GuHCl having a final concentration of $2\times10^{-3}$ mol/L.

Specific Amplification Method was Shown as Follow:

a) the single cell was lysed in an ALB reaction system at room temperature for 3 min, to release chromosomal DNA, then 10, of the GuHCl solution having a concentration of $8\times10^{-3}$ (mol/) was add, allowing for reaction at room temperature for 15 minutes.

b) 2.5 µL of buffer D1 was then added in to a), and place at room temperature for 3 min for denaturing the chromosomal DNA. 5 µL of buffer N1 was then added to stop reaction of denature by neutralizing buffer D1, and finaly being place at room temperature.

c) preparation of MDA reaction system

TABLE 6

REPLI-g kit of Qiagen company (40 µL reation liquid/sample)

| | |
|---|---|
| $ddH_2O$ | 10 µL |
| Reaction buffer | 29 µL |
| REPLI-g DNA polymerase | 1 µL |

The above MDA reaction liquid was added into a 200 µL PCR tube containing 10 µL of DNA template to be stopped denaturing, and then mixed evenly.

d) MDA amplification using PCR apparatus.

The PCR tube was incubated at 30° C. of room temperatue for 16 hours, then incubated at 65° C. for 10 minutes to inactive Phi29 polymerase. The obtained final sample was then place at 4° C. for temporary conservation, or place at −20° C. for extended conservation.

target bands appeared, a next step of Solexa DNA library construction may be performed, and sequenced on computer.

1.4.1 Assaying the Concentration of MDA Amplification Product by Qubit a) firstly ensuring Quant-iT™ buffer and Quant-iT™ reagent to balance to room temperature before use, in which two tubes of standards were taken from the 4° C. refrigerator before use.

b) preparing enough 0.5 mL PCR tubes spedific for Qubit assay; establishing a standard curve using two PCR tube containing the two standards respectively, each sample corresponding to one PCR tube.

c) preparing Quant-iT™ Working Solution: diluting the Quant-iT™ reagent to 1/200 of the original concentration using the Quant-iT™ buffer, in which each 200 µL of Working Solution being suitable for one sample or one standard.

d) preparing the standard and sample solution (Table. 7)

TABLE 7

| | Standard | Sample |
|---|---|---|
| Working Solution | 190 µL | 199 µL |
| Standard | 10 µL | |
| Sample | | 1 µL |
| Total Volume | 200 µL | 200 µL | e) shaking evenly, spinning down for a while, and then incubating at room temperature for 2 minutes.

f) inserting the tubes into a chamber, taking a data on Qubit™ fluorometer, in which the Qubit™ fluorometer was set as selecting Calculate sample concentration, inputing the sample volume, by which the Qubit™ fluorometer would automatically produce a concentration of the original sample, and the amplified product of which the concentration greater than 80 ng/μL was regarded as qualified.

1.4.2 Detection of DMA Amplification Effect Using Housekeeping Gene

PCR:

a) selecting a sample having a qualified concentration assayed by Qubit as housekeeping gene, diluting the sample to be amplified to about 20 μg/mL using ddH₂O, in which each pair of primers needed 2 μL of template.

b) PCR system for detecting housekeeping gene (20 μL/target gene)

TABLE 8

| Reagent | Volume |
| --- | --- |
| ddH₂O | 12.8 μL |
| 10X buffer | 2.0 μL |
| 2.5 mM dNTP | 2.0 μL |
| DNA template | 2.0 μL |
| (forward + reverse) primer | (0.5 + 0.5) μL |
| rTaq enzyme | 0.2 μL | c) amplification on PCR apparatus

| | | |
| --- | --- | --- |
| | 95° C. | 4 min |
| | 32 cycles of | |
| { | 95° C. | 40 s |
| | 55° C. | 30 s |
| | 72° C. | 30 s |
| | 72° C. | 10 min |
| | 4° C. | ∞ |

Electrophoresis: detecting the amplified prodecting using 2% agarose gel electrophoresis; taking an image after being treated with EB staining. After detection of housekeeping gene, if there are 70% housekeeping genes of the target bands in the sample appeared, a next step of Solexa DNA library construction may be performed, and sequenced on computer.

1.5 Sequencing on Computer

The obtained amplified product was sequenced on an Illumina Solexa sequencer in accordance to an online method of a standard protocol of the Next-Generation sequencing technique (http://seqanswers.com/forums/showthread.php?t=21), The sequencing scheme was: three of 5× for the single cell sequencing, ten of 2× (combiding 5×) for determining heterozygosis SNP of the individual, two hundreds of 0.2× (combiding 5×, 2×) for constructing a genetic map using a whole genome.

1.6 Data Analysis

After obtaining the off-computer data by sequencing, Hg19 in human public database was taken as a reference for SNP detection, in details:

a) establishing an index by taking Hg19 (http://hgdownload.cse.ucsc.edu) as a control, aligning the off-computer data by sequencing to the index by a nucleic adic sequence alignment software which used an algorithmic of Burrows Wheeler Transformation compression index (Li, R. et al. SOAP2: an improved ultrafast tool for short read alignment. *Bioinformatics*. 2009, 25, 1966-7), in which parameters were set as blow: −m 100 −x 888 −s 35 −l 32 −v 3 −p 4, to obtain an aligned result. The meaning of each parameter and parameter setting under different conditions could refer to detailed specification online (http://soap.genomics.org.cn/soapaligner.html).

b) taking a fasta document of human Hg19 and Hg19 dbSNP as a reference, subjecting the aligned result to SNP detection by SOAPsnp (parameter settings: −L 100 −u −m −r 0.0010 −2), to obtain a cns document of call SNP result. The meaning of each parameter and parameter setting under different conditions could refer to detailed specification online (http://soap.genomics.org.cn/soapaligner.html).

c) further treatment of the cns document: screening the site quality and p value (Q≥20, and P-value <0.05), to obtain a liable SNP site; integrating SNP results of different single cells into one file, to obtain a statistical result comprising every SNP site genotype of all single cells.

d) by means of maximum parsimony of recombination (MPR), deducing genotypes of two chromosomes from a male parent and a female parent respectively in the case of minimal recombination events, to determine male parent a/female parent b typing results of every single cell.

e) for every SNP genotype results after typing, dividing a chromosome into linkage regions (bin): the SNP number comprising continuous same a or b was at least 5; a physical length of a selected linkage region was greater than 250 kb; other SNP sites which were not meet the standard of dividing were replaced by "missing".

f) after obtaining a bin type, calculating a variation ratio of a/b to obtain a recombination rate between every two continuous bins, the formula was shown below:

recombination rate=the number of recombined single cells/(the number of recombined single cells+the number of parent single cells)

in which the number of recombined single cells referred to the different number of single cell of the two continuous bins with the parent (a/b), the number of parent single cells referred to consistent number of single cells of the two continuous bins with the parent (a/b). Then information of all cells was subjected to a statistical test, to obtain a document of chr*.genetic_distance in flow chart by integrating, which comprised a basic information such as recombination rate, physical distance, specific coordinate range between all two continuous bins.

Figure 4:
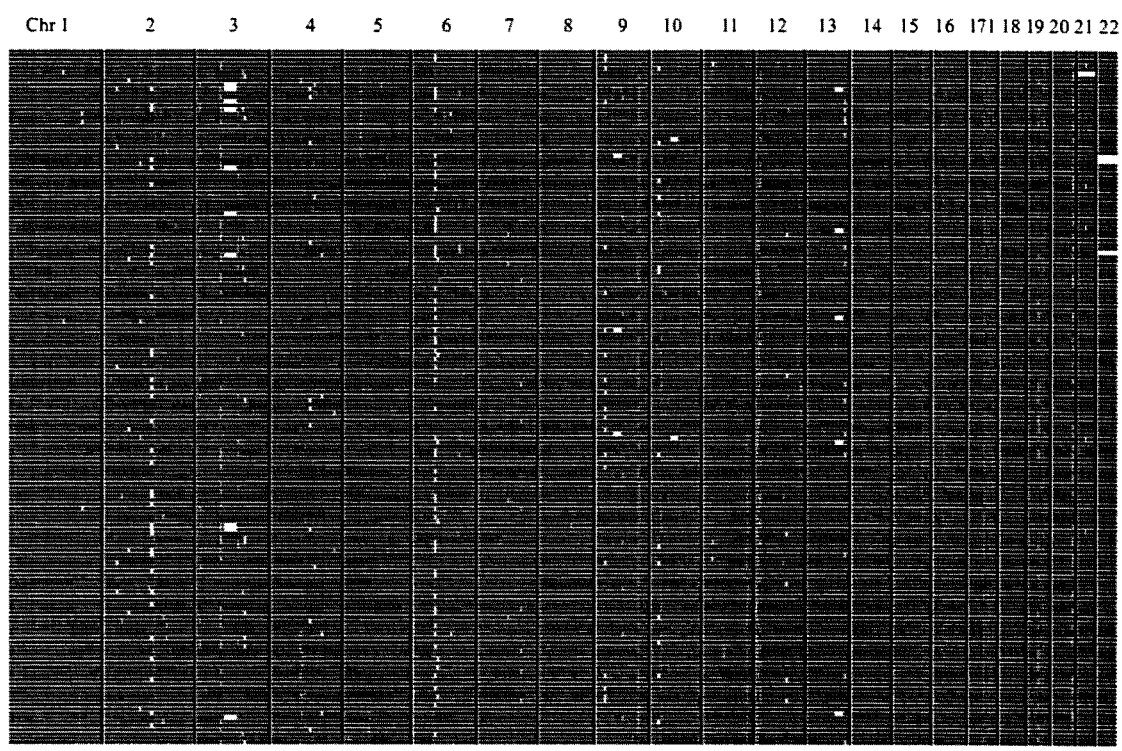
FIG. 4 is a statistical result of a recombination between linkage regions (bins) of a whole genome derived from a single sperm cell (i.e. a recombination map), in which each line represents one sperm cell, two colors therein respectively represents the genotyping result (a light color represents a, a deep color represents b), a white region represents a situation of missing appeared in the typing process, a cross-over point between the light color and the deep color shown in this figure is one recombination point.
Figure 5:
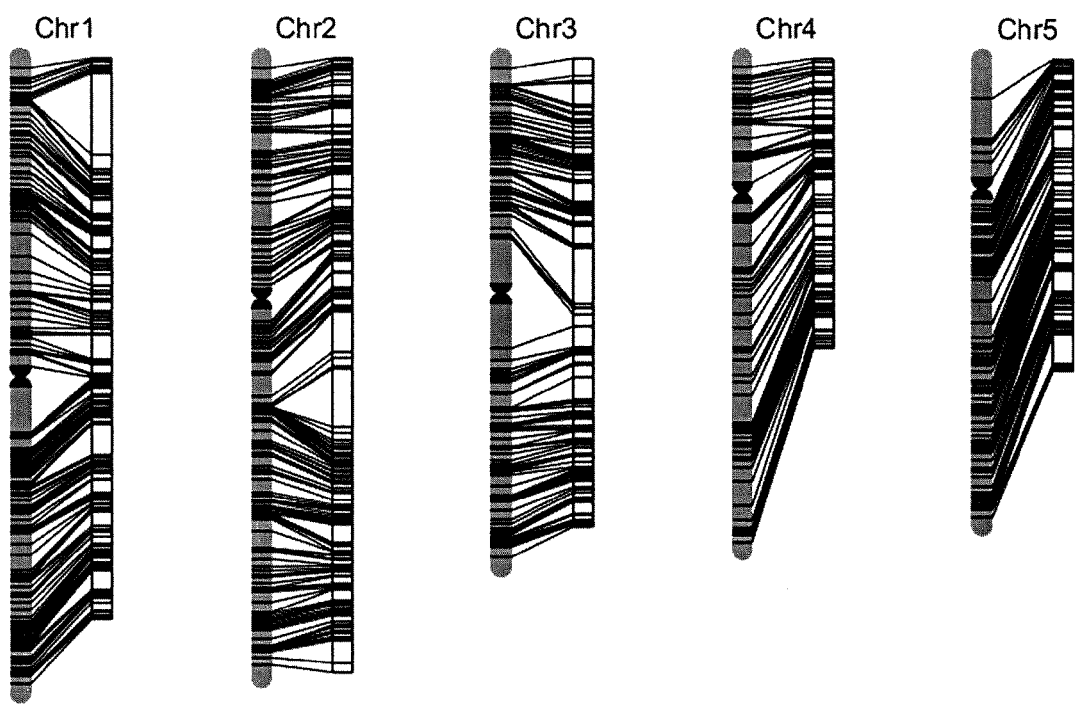
FIG. 5 shows a physical map (left) and a genetic map (right) of Chromosomes 1-5, in which the physical map has a direct expression with a position relationship of each divided linkage region (bin) in the chromosome; the genetic map shows a genetic recombination rate between two continuous bins represented with a unit as cm; for the five chromosomes shown, the actual length and genetic distance of the chromosomes are: chr1 (249.251M, 142.238 cM), chr2 (243.199 M, 155.710 cM), chr3 (198.022 M, 118.738 cM), chr4 (191.154 M, 73.378 cM), chr5 (180.915 M, 78.830 cM)

Finally, based on different color representing different male parent a/female parent b typing result, in which a blank represented a deleting region, a recombination map was obtained, which displayed a statistical result of recombination between bins in the whole genome of almost 200 pairs of single sperm cell, shown in FIG. 4, in which each line represented one single sperm cell, two colors therein respectively represented the genotyping result (for example: a light color represents a, a deep color represents b), a white region represented a situation of missing appeared in the typing process, a cross-over point between the light color and the deep color shown in this figure is one recombination point; according to each combination site one slitting line was made, the tangent point information of each different tangent line was subjected to a statistical test, then a recombination rate of each recombination point could be obtained, for making a genetic map.

making a at each breakpoint, subjecting all obtained non-repetitive tangent points to a statistical test of recombination number, which may obtain a genetic map.

according to breakpoint information (color switching point) of the recombination map, a slitting line at each breakpoint was made, all obtained non-repetitive tangent points were subjected to a statistical test of recombination number, which could obtain a genetic map. FIG. 5 was a genetic map of partial chromosomes, for each chromosome the left was a physical map having one direct expression of a position relationship of each divided region (bin) on the chromosome, the right was a genetic map indicated a genetic recombination rate between every two continuous bins represented with a unit as cm. For the five chromosomes shown, the actual length and genetic distance of the chromosomes were: chr1 (249.251M, 142.238 cM), chr2 (243.199 M, 155.710 cM), chr3 (198.022 M, 118.738 cM), chr4 (191.154 M, 73.378 cM), chr5 (180.915 M, 78.830 cM), the relation and distinguish between the genetic map and the physical map could be clearly and directly understood from FIG. 5.

By such method, the data output was shown below (FIG. 6): within the range of the human whole genome in this case, a total of 1603 haplotype blocks had been determined, with an average length of about 1.5 Mb; a genetic map having a size of 1742.77 cM was constructed; based on this map, 9 unassembled scaffolds and 21 specific sequences had been plotted according to Hg19; 5749 breakpoints and 103 recombination hot spots had been found out in the whole genome.

The obtained recombination map and genetic map constructed according to the method of the present example, an accurate diagnosis could be made with genes closely related to a genetic disease or characteristics more concerned by people in the sampled individual (male), which may predict some characteristics might appeared in the progeny of the male, guiding the proliferation and predicting a risk of related genetic disease.

For example, for analyzing some quality trait loci (QTL), an analysis of sex determination QTL was performed: 122 Y sperm cells and 45 X sperm cells were found out in 167 single sperm cells, which suggested some features of the sperm activity of the male to some extent.

EXAMPLE 2

Searching Recombination Hot Spots by Single Sperm Cell Sequencing, and Analysis of a Haplotype A recombination map and a genetic map were obtained according to step in example 1.

A region commonly having a recombination (a region having high recombination rate) or a region having low-frequency recombination (a region barely occurring recombination) were found out by observation, i.e. the changing point of color distribution in the recombination map.

For studying hot spot region of recombination, relevant sequence and gene were extracted back in gff document of Hg19, which may obtain more elaboration regarding some genes closely related to recombination, so as to verify the scientificity and feasibility of the solution of the present disclosure. As can be seen from FIG. 5, 103 recombination hot spots were found out, some genes related thereof (a total of 50 genes such as ADAMTS18, PRDM9, ADAM12) were found out according to gff document of Hg19, it was already known that PRDM9 gene was able to control the activity of the recombination hot spots in a mammal (for example human) (Prdm9 controls activation of mammalian recombination hotspots. *Science.* 2010, 327, 835); the mutation of MED1 gene could lead to structure changes of chromosome, which may result in decrease of recombination rate (Rockmill, B. & Roeder, GS. The yeast med1 mutant undergoes both meiotic homolog nondisjunction and precocious separation of sister chromatids. *Genetics* 136, 65-74 (1994)). It illustrated that the information obtained from the recombination map and the genetic map constructed by the method of the present disclosure was liable, which may be used for guiding the preliminary annotation to some genes with unknown functions, for deeper genomics study.

Figure 6:
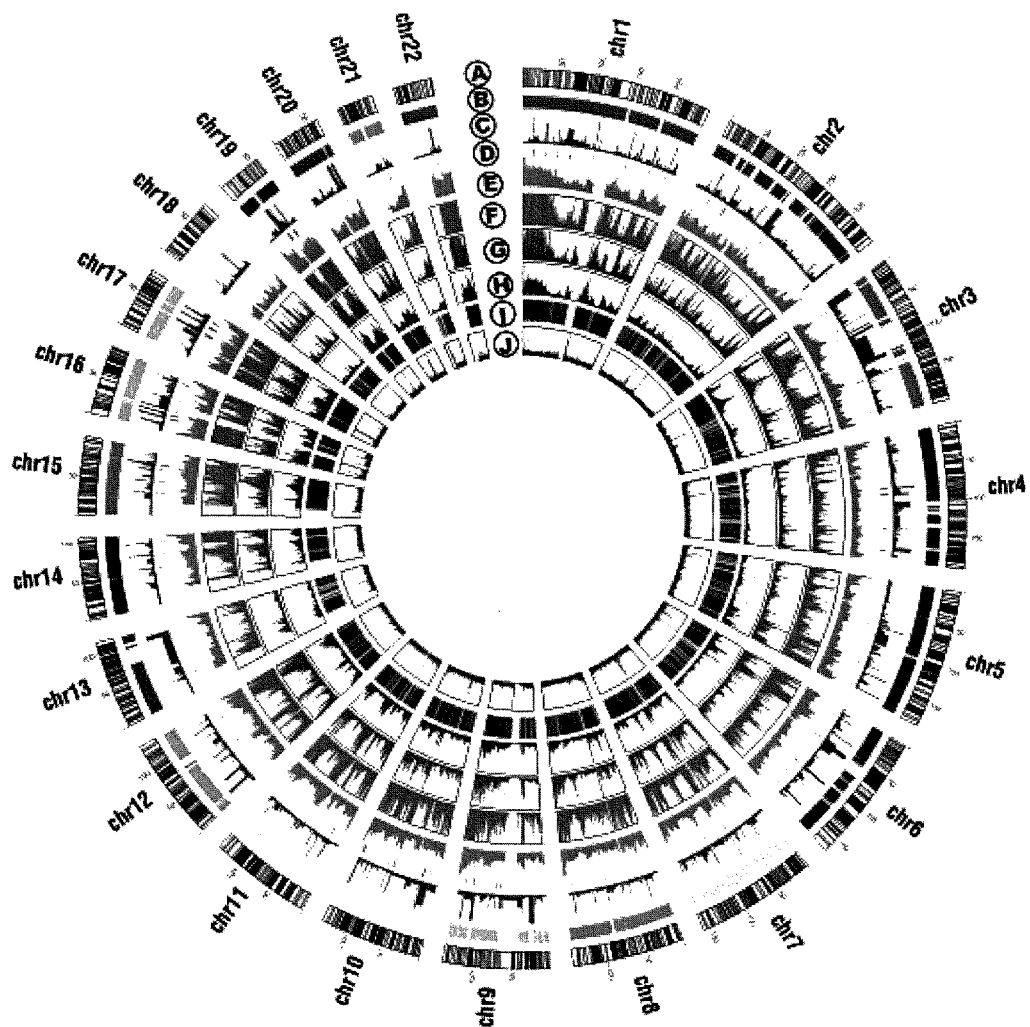
FIG. 6 is an output figure of analyzing data of a whole genome derived from a single sperm cell, A represents the No. of chromosome, B represents haplotype blocks, C represents a value of the genetic distance (cm), D represents a hot spot, E represents a GC content, F represents a genome derive from a sperm cell having a coverage of 5×, G represents a genome derive from a sperm cell having a coverage of 2×, H represents a genome derive from a sperm cell having a coverage of 0.2×, I represents a genetic density in an sequential order from the low to the high represented with colors from the light color to the deep color, J represents a SNP density.

For studying regions closely linked in genetic, the method of the present disclosure could obtain a preliminary analysis result of haplotype. FIG. 6, integrated data results obtained in Example 1, comprised haplotype blocks of each chromosome, corresponding genetic distance represented with a length unit as cm, annotation of hot spot region of recombination, coverage, gene density, SNP desity, and the like. As can be seen from FIG. 6, chr1 (Chromosome 1) had the maximal number of SNP (29, 291), while chr18 had the minimal number of SNP (2,992), the total number of SNP was 233,030; for statistics of haplotype blocks, chr2 had the maximal number (160), while chr22 had the minimal number (18), the total number of haplotype blocks was 1,603. The obtaining of the information of conservatism in close genetic region was benefit for study on whether these close genetic regions were closely related with the basic life activity of human beings, if not, whether the close genetic would generate severe consequence and the like.

INDUSTRIAL APPLICABILITY

The method and the device of constructing a genetic map, and the method and the device of determining a haplotype may be effectively applied to a mammal, particularly to construction of a human genetic map, as well as the determination and analysis of a haplotype of a single cell Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A method of constructing a genetic map, comprising the following steps:

whole genome sequencing with a sequencing unit at least one single cell derived from a human, to obtain whole genome sequencing data of each of the at least one single cell wherein sequencing comprises lysing the single cell using a subunit to release the whole genome DNA with an alkaline lysis method;

aligning with a statistical unit connected to the sequencing unit the whole genome sequencing data of each of the at least one single cell to a reference sequence respectively to determine SNP site genotypes of each of the at least one single cell;

deducing with a parent typing unit connected to the statistical unit genotypes of two chromosomes from a male parent and a female parent respectively, based on the SNP site genotypes of each of the at least one single cell by means of a maximum parsimony of recombination to determine male parent a/female parent b typing results of SNP genotype of each of the at least one single cell;

dividing with a linkage region dividing unit connected to the parent typing unit a chromosome of the species into linkage regions based on the male parent a/female parent b typing results of SNP genotype of each of the at least one single cell, wherein a standard of dividing the chromosome of the species into linkage regions is that: (1) the SNP number comprising continuous same a or b is at least 5; (2) a physical length of a selected linkage region is greater than 250 kb;

obtaining with a calculation unit a recombination rate between two continuous linkage regions by determining a variation ratio of a/b between two continuous linkage regions for each one of the at least one single cell;

determining a recombination map for each one of the at least one single cell, the recombination map comprising the recombination rate between each two continuous linkage regions wherein a boundary site between a and b is a recombination site; and constructing a genetic map of the human by determining a recombination rate of each recombination site from the recombination map for each of the at least one single cells.

2. The method of claim 1, wherein the whole genome sequencing is performed using a Next-Generation or a Third-Generation sequencing platform.

3. The method of claim 1, wherein the reference sequence is a known genomic sequence of the species.

4. A device for constructing a high resolution genetic map, comprising:
   a single cell whole genome sequencing unit configured for whole genome sequencing for at least one single cell derived from a human, to obtain whole genome sequencing data of each of the at least one single cells;
   an SNP site genotype statistical unit connected to the single cell whole genome sequencing unit and configured for aligning the whole genome sequencing data of each of the at least one single cell to a reference sequence respectively to determine SNP site genotypes of each of the at least one single cell;
   a parent typing unit connected to the SNP site genotype statistical unit and configured for deducing genotypes of two chromosomes from a male parent and a female parent respectively by means of a maximum parsimony of recombination based on the SNP site genotypes of each of the at least one single cell, to determine male parent a/female parent b typing results of SNP genotype of each of the at least one single cell;
   a linkage region dividing unit connected to the parent typing unit and configured for dividing a chromosome of the species into linkage regions based on the male parent a/female parent b typing results of SNP genotype of each of the at least one single cell, wherein a standard of dividing the chromosome of the species into linkage regions is that: (1) the SNP number comprising continuous same a or b is at least 5; (2) a physical length of a selected linkage region is greater than 250 kb;
   a recombination rate between contiguous linkage regions calculating unit connected to the linkage region dividing unit and configured for determining a variation ratio of a/b between two continuous linkage regions, to obtain a recombination rate between every two continuous linkage regions for each of the at least one single cells, and determining the recombination map of each of the at least one single cell based on the recombination rate between every two continuous linkage regions, wherein a boundary site between a and b is a recombination site;
   a recombination rate of the recombination site calculating unit connected to the recombination rate between contiguous linkage regions calculating unit and configured for determining a recombination rate of each recombination site to construct the genetic map of the species based on recombination maps of all single cells.

5. The device of claim 4, wherein the single cell whole genome sequencing unit further comprises:
   a cellular whole genome DNA obtaining subunit configured for lysing the single cell to release a whole genome DNA using an alkaline lysis method;
   a whole genome DNA amplifying subunit connected to the cellular whole genome DNA obtaining subunit and configured for amplifying the whole genome DNA, to obtain an amplified whole genome DNA; and
   a whole genome DNA sequencing subunit connected to the whole genome DNA amplifying subunit and configured for constructing a sequencing-library for the amplified whole genome DNA, to obtain a sequencing-library of the single cell, and sequencing the sequencing-library of the single cell, to obtain the every whole genome sequencing data of the at least one single cell.

6. The device of claim 4, wherein the cellular whole genome DNA obtaining subunit is further suitable for subjecting the released whole genome DNA to a guanidine hydrochloride treatment after the single cell is lysed to release a whole genome DNA, wherein the whole genome DNA sequencing subunit is suitable for using at least one of a Next-Generation and a Third-Generation sequencing platform.

7. A method of determining a haplotype of a single cell, comprising following steps:
   whole genome sequencing with a first unit the single cell to obtain a whole genome sequencing data of the single cell;
   aligning with a second unit connected to the first unit the obtained whole genome sequencing data to a reference sequence; to determine SNP site genotypes of the single cell;
   deducing with a third unit connected to the second unit genotypes of two chromosomes from a male parent and a female parent respectively by means of a maximum parsimony of recombination based on the SNP site genotypes of the single cell to determine male parent a/female parent b typing results of the SNP site genotypes of the single cell;
   dividing with a fourth unit connected to the third unit a chromosome of the species into linkage regions based on the male parent a/female parent b typing results of the SNP site genotypes of the single cell, wherein a standard of dividing the chromosome of the species into linkage regions is that: (1) the SNP number comprising continuous same a or b is at least 5; (2) a physical length of a selected linkage region is greater than 250 kb;
   determining with a fifth unit the haplotype of the single cell based on the determined linkage region wherein a set of a or b in the same linkage regions of the whole genome constitutes the haplotype of the single cell.

8. The method of claim 7, wherein the single cell derives from a mammal.

9. The method of claim 7, wherein the single cell is a germ cell, and the germ cell is a sperm cell.

10. The method of claim 7, wherein the whole genome sequencing is performed using a Next-Generation or a Third-Generation sequencing platform.

11. The method of claim 7, wherein the step of whole genome sequencing the single cell, to obtain a whole genome sequencing data of the single cell further comprises:

lysing with a DNA obtaining subunit the single cell to release a whole genome DNA using an alkaline lysis method;

amplifying with a DNA amplifying subunit the whole genome DNA, to obtain an amplified whole genome DNA;

constructing a sequencing-library for the amplified whole genome DNA to obtain a sequencing-library of the single cell; and sequencing the sequencing-library of the single cell, to obtain the whole genome sequencing data of the single cell, wherein the single cell is a sperm cell, after the single cell is lysed to release a whole genome DNA, the whole genome DNA is subjected to a guanidine hydrochloride treatment, and the guanidine hydrochloride treatment is performed using a solution of guanidine hydrochloride having a concentration of $2\times10^{-3}$ to $3\times10^{-1}$ mol/L.

12. The method of claim 11, wherein the single cell derives from human, and the solution of guanidine hydrochloride having a concentration of $2\times10^{-3}$ mol/L.

13. The method of claim 7, wherein the reference sequence is a known genomic sequence of the species.

14. A device for determining a haplotype of a single cell, comprising:

a single cell whole genome sequencing unit configured for whole genome sequencing the single cell, to obtain a whole genome sequencing data of the single cell;

an SNP site genotype statistical unit connected to the single cell whole genome sequencing unit and configured for aligning the obtained whole genome sequencing data to a reference sequence, to determine SNP site genotypes of the single cell;

a parent typing unit connected to the SNP site genotype statistical unit and configured for deducing genotypes of two chromosomes from a male parent and a female parent respectively by means of a maximum parsimony of recombination based on the SNP site genotypes of the single cell, to determine male parent a/female parent b typing results of the SNP site genotypes of the single cell;

a linkage region (bin) dividing unit connected to the parent typing unit and configured for dividing a chromosome of the species into linkage regions (bin) based on the male parent a/female parent b typing results of the SNP site genotypes of the single cell, wherein a standard of dividing the chromosome of the species into linkage regions is that: (1) the SNP number comprising continuous same a or b is at least 5; (2) a physical length of a selected linkage region is greater than 250 kb;

a haplotype determining unit, connected to the linkage region dividing unit and configured for determining the haplotype of the single cell in a determined linkage region, wherein a set of a or b in the same linkage regions of the whole genome constituents the haplotype of the single cell.

15. The device of claim 14, wherein the single cell whole genome sequencing unit further comprises:

a cellular whole genome DNA obtaining subunit configured for lysing the single cell to release a whole genome DNA using an alkaline lysis method;

a whole genome DNA amplifying subunit connected to the cellular whole genome DNA obtaining subunit and configured for amplifying the whole genome DNA, to obtain an amplified whole genome DNA; and a whole genome DNA sequencing subunit connected to the whole genome DNA amplifying subunit and configured for constructing a sequencing-library for the amplified whole genome DNA, to obtain a sequencing-library of the single cell, and sequencing the sequencing-library of the single cell, to obtain the whole genome sequencing data of each of the at least one single cell.

16. The device of claim 15, wherein the cellular whole genome DNA obtaining subunit is further suitable for subjecting the released whole genome DNA to a guanidine hydrochloride treatment after the single cell is lysed.

17. The device of claim 15, wherein the whole genome DNA sequencing subunit is suitable for using at least one of a Next-Generation and a Third-Generation sequencing platform.

\* \* \* \* \*